United States Patent [19]

Strehlke et al.

[11] Patent Number: 4,916,144
[45] Date of Patent: Apr. 10, 1990

[54] N-SUBSTITUTED IMIDAZOLES AS AROMATASE INHIBITORS

[75] Inventors: Peter Strehlke; Rolf Bohlmann; David Henderson; Yukishige Nishino, all of Berlin, Fed. Rep. of Germany

[73] Assignee: Schering Aktiengesellschaft, Fed. Rep. of Germany

[21] Appl. No.: 331,283

[22] Filed: Mar. 31, 1989

[30] Foreign Application Priority Data

Mar. 31, 1988 [DE] Fed. Rep. of Germany ....... 3811574

[51] Int. Cl.⁴ ................. A61K 31/445; A61K 31/415; C07D 233/60; C07D 233/61
[52] U.S. Cl. .................................... 514/326; 514/397; 514/399; 546/210; 548/335; 548/336
[58] Field of Search ................ 548/335, 336; 514/399, 514/397, 326; 546/210

[56] References Cited
PUBLICATIONS

Strehlke et al., *Eur. J. Med. Chem.-Chimica Therapeutica*, May-Jun., 1979, 14, No. 3, pp. 231-237.

*Primary Examiner*—Richard A. Schwartz
*Attorney, Agent, or Firm*—Millen, White & Zelano

[57] ABSTRACT

The invention relates to N-substituted imidazoles of the formula,

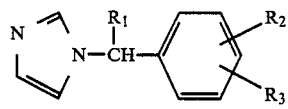

processes for their production as well as their use in pharmaceutical agents.

The compounds according to the invention have aromatase-inhibiting properties and are suitable for therapy of estrogen-caused diseases.

13 Claims, No Drawings

N-SUBSTITUTED IMIDAZOLES AS AROMATASE INHIBITORS

SUMMARY OF THE INVENTION

This invention relates to N-substituted imidazoles, processes for their production as well as their use in pharmaceutical agents.

The compounds according to the invention are described by general formula I

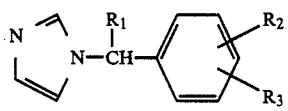

in which $R_1$ is a hydrogen atom, a saturated or unsaturated, straight-chain or branched-chain hydrocarbon radical with 1 to 10 carbon atoms or a cyclic hydrocarbon radical with 3 to 9 carbon atoms or a cycloalkylalkyl radical with 4 to 12 carbon atoms or an arylalkyl radical with 7 to 12 carbon atoms, $R_2$ is an optionally substituted benzyloxy group, $R_3$ is a cyano group, an optionally substituted alkanoyl group with 2 to 10 carbon atoms, an optionally substituted benzoyl group or an optionally derivatized carboxyl group.

The compounds of general formula I can also be present in the form of their salts.

The saturated or unsaturated straight-chain or branched-chain hydrocarbon radicals with 1 to 10 carbon atoms suitable as the radical $R_1$ include, e.g., alkyl, alkenyl, for example, the methyl, ethyl, propyl, propenyl, isopropyl, butyl, hexyl, octyl and decyl radical. Propyl is preferred. The cyclic hydrocarbon radical includes all those with 3 to 9 carbon atoms. Exemplary cycloalkyl radicals include, e.g., cyclopentyl and cyclohexyl radical. The cycloalkylalkyl radicals include all those with 4 to 12 carbon atoms, including, e.g., cyclopentylmethyl, cyclohexylmethyl radical, etc. Arylalkyl radicals include all those with 7-10 carbon atoms, e.g., benzyl.

The optionally substituted benzyloxy groups, suitable as radical $R_2$, can contain, as substituents on the aromatic substance, one or more halogen atoms (e.g., chlorine, fluorine, bromine and iodine), $C_{1-4}$ alkyl, hydroxyl, methoxy, amino and cyano groups. When substituted, the benzyloxy group can be substitute singly or repeatedly (e.g., 1-3 times) with substituents which can be the same or different. 3-bromo, 4-bromo, 4-chloro, 2,3-, 2,4-, 4,5- and 4,6-dichloro-benzyloxy groups are preferred as substituted benzyloxy groups.

The optionally substituted alkanoyl groups suitable as radicals $R_3$ are those with 2 to 10 carbon atoms. For example, this alkanoyl group can be straight-chain or branched-chain and be substituted singly or repeatedly (e.g., 1-3 times) with the same or different substituents on the chain. Acetyl, propanoyl, butyryl, valeryl and caproyl groups can be mentioned as preferred alkanoyl groups.

Halogen atoms (e.g., chlorine, fluorine, bromine and iodine), methoxy, amino, hydroxyl and cyano groups are suitable as substituents of the alkanoyl group.

$R_3$ can also be an optionally substituted benzoyl group. When substituted, the benzoyl group may be substituted singly or repeatedly (e.g., 1-3 times) with the same or different substituents. Suitable substituents include, e.g., halogen atoms (e.g., chlorine, fluorine, bromine and iodine), $C_{1-4}$ alkyl, methoxy, amino, hydroxyl and cyano groups.

Further, $R_3$ has the meaning of an optionally derivatized carboxyl group. When the carboxyl group is derivatized, suitable derivatives include carboxylic acid, $C_{1-6}$ alkyl carboxylic acid esters and carboxylic acid amides (e.g., mono- or di-$C_{1-6}$-alkylamides, anilides or

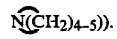

Methyl, ethyl and butyl ester as well as carboxylic acid amide, carboxylic acid isopropylamide, carboxylic acid anilide and pyrrolidinylamide are particularly preferred.

The radicals $R_2$ and $R_3$ can be in all suitable positions of the phenyl ring.

As possible salts of the compounds of general formula I there can be mentioned physiologically compatible salts of organic or inorganic acids. The malonate, succinate, hydrochloride and hydrobromide are especially suitable as salts.

The compounds of general formula I are inhibitors of estrogen biosynthesis (aromatase inhibitors). Therefore they are suitable for treating diseases which are caused by estrogens or are dependent on estrogens. Thus they are suitable for treating estrogen-induced or estrogen-stimulated tumors, such as, for example, breast cancer or prostate hyperplasia (The Lancet, 1984, 1237–1239).

The compounds according to the invention are also valuable for affecting fertility. Thus, male infertility, which results from increased estrogen levels, can be eliminated with the new active compounds.

Further, the compounds can be used in women in the reproductive age as a birth control agent to inhibit ovulation by estrogen deprivation.

Aromatase inhibitors are also suitable for treating imminent myocardial infarction, since increased estrogen levels can precede a myocardial infarction in males (see, e.g., U.S. Pat. No. 4,289,762).

Besides steroids, known substances exhibiting aromatase-inhibiting action are also nonsteroidal substances; such as, for example, the various nitrogen heterocycles described in the European patent applications, publication numbers 0165777 to 0165784, the substituted glutaric acid imides described in J. Med. Chem. 1986, 29, pages 1362–1369, the substituted imidazopyridines described in the European patent application, publication number 0165904 and the substituted heterocyclically substituted toluene nitriles described in the European patent application, publication number 0236940.

The compounds of this application are distinguished in that they selectively inhibit the enzyme system of the aromatase and do not adversely affect other enzyme systems in an appreciable manner.

The invention further relates to the use of already known compounds of formula Ia with $R_3$ corresponding to the formula I denoted as $R_{3a}$ and having the meaning of a nitro or amino group as aromatase inhibitor. These compounds are described as antifungally effective substances in Eur. J. Med. Chem., 1979 (14), pages 231–237, and in German laid-open specification 24 18 502. The aromatase-inhibiting action of these known compounds is distinguished in that they selectively inhibit the aromatase enzyme system.

As compounds known from literature, which especially selectively inhibit aromatase, there can be mentioned, for example, 4-nitro-2-(l-(1-imidazolyl)butyl)-phenyl)-(2,4-dichlorobenzyl)-ether, hydrochloride, 4-amino-2-(1-(1-imidazolyl)-butyl)phenyl-(2,4-dichlorobenzyl)-ether, hydrochloride and (2,4-dichlorobenzyl)-(2-(1-imidazolyl-methyl)-4-nitrophenyl)-ether.

The enzymatic activities of the comparison compound 2,4-dichlorobenzyl-{2-[1-(1-imidazolyl)-butyl]-phenyl)ether (EP-A 0165 777) as well as the two compounds according to the invention 4-[1-(1-imidazolyl-butyl]-3-(2,4-dichlorobenzyloxy)-benzonitrile (compound 1) and 3-(4-bromobenzyloxy)-4-[1-(1-imidazolyl)-butyl]benzanilide (compound 2) is determined with the biological test described below.

The capabilities of compounds to inhibit the enzyme system of aromatase is tested on microsomes obtained from human placenta. The release of tritium-labeled water ($^3H_2O$), which is released as reaction product in the aromatizing of (1beta-$^3H$) androstenedione to estrogen, is measured according to the method of Thompson and Siiteri (J. Biol. Chem. 249, 5364–72 (1974). The corresponding inhibition values ($K_1$, aromatase) are determined according to the method of Dixon (Biochem. J.94, 760 (1965) by graphic determination of the application of 1/v against the inhibition concentration.

|  | $k_i$ Aromatase |  |
| --- | --- | --- |
| Comparison compound | 4.5 | nmol/L |
| Compound 1 | 0.11 | nmol/L |
| Compound 2 | 0.64 | nmol/L |

The amount of the compounds to be administered varies within a wide range and can cover any effective amount. Depending on the condition to be treated and the kind of administration, the amount of compounds administered can be 0.0001–10 mg/kg of body weight, preferably 0.0001–0.1 mg/kg/day, preferably 0.001–1 mg/kg of body weight.

The dosage is 0.0001–10 mg/kg/day, preferably 0.0001–1 mg/kg/day, analogous to the known agent aminoglutethimide when administered to treat estrogen-stimulated tumors, 0.0001–10 mg/kg/day, preferably 0.0001–1 mg/kg/day when administered analogous to the known agent aminoglutethimide to treat male infertility, 0.0001–10 mg/kg/day, preferably 0.0001–1 when administered analogously to the known agent 4-hydroxy-4-andro-stene-3,17-dione to inhibit ovulation, and 0.001–3 mg/kg/day, preferably 0.01–2 when administered analogously to the known agent 4-hydroxy-4-androstene-3,17-dione for the treatment of imminent myocardial infarction.

For the treatment of estrogen-stimulated tumors, a dosage range of 0.005–0.05 mg/kg/day is mostly preferred.

In a particularly preferred embodiment, when $R_{3a}$ is nitro or amino, for all indications the dosage is less than 100 mg per patient per day, preferably less than 10 mg per patient per day. The range is 0.0001–0.1 mg/kg/day, preferably 0.0001–0.05, or 0.000–0.01 mg/kg/day.

Capsules, pills, tablets, dragees, etc. are suitable for oral administration. Besides the active ingredient, the dosage units can contain a pharmaceutically compatible vehicle, such as, for example, starch, sugar, sorbitol, gelatin, lubricant, silicic acid, talc, etc. The individual dosage units for oral application can contain, for example, 0.05–50 mg of active ingredient (aromatase inhibitor).

For parenteral administration the active ingredients can be dissolved or suspended in a physiologically compatible diluent. For example, oils with or without addition of a solubilizer, a surfactant, a suspension or emulsion mixture is used as diluent. As examples for the oils used there can be mentioned: olive oil, peanut oil, cottonseed oil, soybean oil, castor oil and sesame oil.

The compounds can also be used in the form of a depot injection or an implant preparation, which can be formulated so that a delayed active ingredient release is made possible.

Implants can contain as inert materials, for example, biodegradable polymers or synthetic silicones, such as, for example, silicone rubber. Moreover, the active ingredients can be worked, for example, into plasters for percutaneous application.

Thus the invention also relates to pharmaceutical preparations and the use of the compounds for the production of these preparations for treatment of estrogen-caused diseases.

The invention further relates to processes for the production of substituted imidazoles of general formula I given above, characterized in that (a) a compound of general formula II

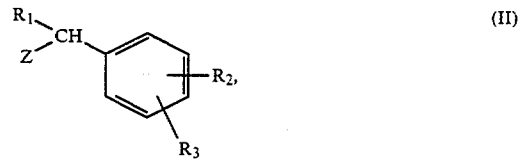

in which $R_1$, $R_2$ and $R_3$ have the meaning mentioned in formula I above, and Z means a leaving group, is reacted with a compound of general formula III

in which

M means a hydrogen atom or an alkali metal atom, or (b) a compound of general formula IV

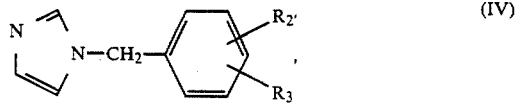

in which $R_2$ has the same meaning as $R_2$ in formula I provided that $R_2$ is an electrophilic, nondeprotonatable radical, as well as $R_3$ has the meaning given above, is reacted, with a compound of general formula V

in which $R_1$ has the meaning mentioned in formula I, and

Z means a leaving group, or (c) a compound of general formula VI

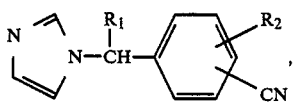

in which

R$_1$ and R$_2$ have the meaning mentioned in formula I, is hydrolytically reacted into the carboxyl compound or into the carboxylic acid amide. The carboxyl compound is optionally reacted with an alcohol to form the ester or is reacted with a halogenating agent to form the carboxylic acid halide, which can be reacted with ammonia or with amines into the carboxylic acid amide or into the substituted carboxylic acid amides. A compound of general formula VI can optionally be reacted with an organometallic compound to form the alkanoyl or benzoyl derivative.

Easily substitutable groups, known from the literature, are suitable as leaving groups Z for the reactions mentioned under (a). As such functional groups suitable for leaving group capability can be mentioned, for example, the mesyl, tosyl, triflat and acetyl group. Also the halogens, e.g., chlorine and bromine have proved to be suitable groups. The suitable methods are described, among others, in Eur. J. Med. Chem. 1979, pages 231–237.

The hydrogen atom and alkali metal atoms, for example, are suitable as substituents M of general formula III. Lithium, sodium and potassium are preferred as alkali metal atoms.

The reactions, which are listed under (a), i.e., the reactions of compounds of general formula II with compounds of general formula III, can be performed in all inert organic solvents. For example, dimethylformamide, dimethyl sulfoxide and various ethers (e.g., tetrahydrofuran, dioxane and diethyl ether) are suitable as solvents.

Process (a) can be carried out between −20 and +180° C., preferably between +20 and 50° C. (M=H) and preferably between +100 and +160° C. (M=H).

The production of the compound of general formula I can also be performed according to process b). Compounds of general formula IV are reacted with compounds of general formula V. All usual leaving groups, e.g., those named in (a), are suitable as leaving group Z of the compounds of general formula V.

For the production of the compound of general formula I according to process (b) the corresponding benzyl anion is produced with bases from the compounds of general formula IV (the radical R$_2$ must be electrophilic and must not be deprotonatable) and the anion is reacted by standard methods with the compounds of general formula V. The benzyl —CH$_2$—group in the compounds of general formula IV can be deprotonated by means of bases, for example by reaction with tertiary amines, sodium hydride, lithium hydride or lithium diisopropylamide and magnesium hydride, and with compounds of general formula V.

The reaction may be carried out with or without a solvent at a temperature of −100 to +100° C. When a solvent is used, suitable solvents include inert solvents, such as ethers, e.g., tetrahydrofuran, dioxane and diethylether or dimethylformamide, etc.

The compounds of general formula I according to the invention can also be produced according to process (c). In this case, compounds of general formula VI are reacted according to standard methods.

The cyano compounds can converted under hydrolytic conditions into the carboxylic acid amides or carboxylic acids.

The resulting carboxyl compounds can be reacted with alcohols under standard conditions of esterification into the corresponding carboxylic acid esters.

It is also possible to obtain carboxylic acid esters by the reaction sequence carboxylic acid and carboxylic acid halide. The carboxylic acid halides that can be obtained as intermediate products can be used for the production of carboxylic acid amides. For example, a carboxylic acid chloride can be reacted with ammonia or an amine to the carboxylic acid amide or substituted carboxylic acid amide.

But it is also possible to convert the carboxylic acid ester group into other esters under conditions of a transesterification reaction with alcohols in the presence of an acid, for example, 4-toluenesulfonic acid.

The production of the optionally substituted alkanoyl and benzoyl compounds of general formula I takes place by reaction of compounds of general formula VI with organometallic compounds, for example, Grignard reagents.

Without further elaboration, it is believed that one skilled in the art can, using the preceding description; utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application German P 38 11 574.3, filed Mar. 31, 1988, are hereby incorporated by reference.

EXAMPLES

Example I 4-(2,4-Dichlorobenzyloxy)-3-[1-(1-imidazolyl)-butyl]-benzonitrile

4-Butyryloxybenzonitrile is obtained by esterification of 4-hydroxybenzonitrile with butyric acid chloride and is further reacted by Fries reaction in the presence of aluminum trichloride in nitrobenzene into the 3-butyl-4-hydroxybenzonitrile (melting point: 74°–76° C.). The phenolic hydroxyl group is etherified with 2,4-dichlorobenzyl chloride in the presence of sodium hydride in dimethylformamide to 3-butyryl-4-(2,4-dichlorobenzyloxy)-benzonitrile (melting point: 79°–80° C.). By reduction of the aromatic keto group with sodium boron hydride in aqueous dioxane the 4-(2,4-dichlorobenzyloxy)-3-(1-hydroxybutyl)-benzonitrile (melting point: 120°–121° C.) is obtained. By chlorination of the substituted benzyl alcohol with thionyl chloride the 3-(1-chlorobutyl)-4-(2,4-dichlorobenzyloxy)-benzonitrile (light yellow oil) is obtained. By reaction of the last-named compound with imidazole in the presence of sodium hydride in dimethylformamide at room temperature the 4-(2,4-dichlorobenzyloxy)-3-[1-(1-imidazolyl)-butyl]-benzonitrile is obtained after recrystallization from ether/hexane with a melting point of 132°–133° C.

EXAMPLE 2

4-(3-Bromobenzyloxy)-3-[1-(1-imidazolyl)-butyl]benzonitrile

This compound is obtained analogously to example 1. The 4-(3-bromobenzyloxy)-3-[I-(1-imidazolyl)-butyl]-benzonitrile melts at 117°-118° C.

EXAMPLE 3

4-(4-bromobenzyloxy)-3-[I-(I-imidazolyl)-butyl]benzonitrile

This compound is obtained analogously to example 1. Melting point of 160°-162° C.

EXAMPLE 4

{4-(4-Bromobenzyloxy)-3-[1-(1-imidazolyl)-butyl]-phenyl)-pentyl-ketone

The }4-(4-bromobenzyloxy)-3-[1-(1-imidazolyl)-butyl]-phenyl}-pentyl-ketone is obtained as yellow oil by reaction of the nitrile of example 3 with pentylmagnesium bromide in tetrahydrofuran.

EXAMPLE 5

3-(2,4-Dichlorobenzyloxy)-4-[1-(1-imidazolyl)-butyl]-benzonitrile

3-Bromo-1-butyryloxybenzene is obtained by esterification of 3-bromophenol with butyric acid chloride and further is reacted, by Fries reaction and etherification of the phenolic hydroxyl group, with 2,4-dichlorobenzyl chloride into the 3-(2,4-dichlorobenzyloxy)-4-butyryl-1-bromobenzene. The 3(2,4-dichlorobenzyloxy)-4-butyrylbenzonitrile with a melting point of 97°-98° C. is obtained by reaction of substituted bromobenzene with copper(I) cyanide in N-methyl pyrrolidone (3 hours at 180° C.). The aromatic keto group is reduced with sodium boron hydride in aqueous dioxane to 3-(2,4-dichlorobenzyloxy)-4-(1-hydroxybutyl)-benzonitrile, melting point of 101°-105° C. The 3-(2,4-dichlorobenzyloxy)-4-(1-chlorobutyl)benzonitrile thionyl chloride. The substituted benzyl chloride is reacted with the sodium salt of the imidazole in dimethylformamide to 3-(2,4-dichlorobenzyloxy)-4-(imidazolyl)-butyl]-benzonitrile (melting point of 105°-107° C.).

EXAMPLE 6

3 (4-Bromobenzyloxy)-4-[1-(1-imidazolyl)-butyl]benzonitrile

This compound is obtained analogously to example 5, melting point of 107°-110° C.

EXAMPLE 7

3-(3-Bromobenzyloxy)-4-[1-(1-imidazolyl)-butyl]benzonitrile, hydrochloride

This compound is obtained analogously to example 5 and subsequent conversion of the base into the hydrochloride under standard conditions, melting point of 158°-162° C.

EXAMPLE 8

4-(4-Bromobenzyloxy)-3-[1-(1-imidazolyl)-butyl]-benzoic acid 1.5 g of 4-(4-bromobenzyloxy)-3-[1-(1-imidazolyl)-butyl]-benzonitrile (of example 3) is reacted with 3 g of potassium hydroxide in an aqueous methanol solution for 24 hours under reflux. After working up, 1.1 g of 4-(4-bromobenzyloxy)-3-[1-(1-imidazolyl)-butyl]-benzoic acid with a melting point of 187°-189° C. is obtained.

EXAMPLE 9

4-(4-Bromobenzyloxy)-3-[1-(1-imidazolyl)-butyl]benzanilide

The substituted benzoic acid of example 8 is reacted with thionyl chloride into the acid chloride and further with aniline in a dioxane/tetrahydrofuran mixture into 4-(4-bromobenzyloxy)-3-[1-(1-imidazolyl)butyl]-benzanilide with a melting point of 159°-166° C.

EXAMPLE 10

3-(4-bromobenzyloxy)-4-[1-(1-imidazolyl)-butyl]-benzoic acid

The benzonitrile of example 6, analogously to example 8, is reacted to 3-(4-bromobenzyloxy)-4-[1-(1-imidazolyl)-butyl]-benzoic acid with a melting point of 155°-158° C.

EXAMPLE 11

3-(4-Bromobenzyloxy)-4-[1-(1-imidazolyl)-butyl]-benzanilide

The substituted benzoic acid of example 10, analogously to example 9, is reacted into 3-(4-bromobenzyloxy)-4-[1-(1-imdiazolyl)-butyl]-benzanilide with a melting point of 168° C.

EXAMPLE 12

{3-(4-Bromobenzyloxy)-4-[I-(1-imidazolyl)-butyl]-phenyl}-phenyl-ketone

The substituted benzonitrile of example 8, analogously to example 4, is reacted with pentylmagnesium bromide to (3-(4-bromobenzyloxy)-4-[(1-(1-imidazolyl)-butyl]-phenyl-pentyl-ketone, melting point of 70°-72° C.

EXAMPLE 13

3-(2,4-Dichlorobenzyloxy)-4-[1 (1-imidazolyl)-butyl]benzoic acid

The substituted benzonitrile of example 5, analogously to example 8, is reacted into the 3-(2,4-dichlorobenzyloxy)-4-[1-(1-imidazolyl)-butyl]-benzoic acid.

EXAMPLE 14

3-(2,4-Dichlorobenzyloxy)-4-[1-(1-imidazolyl)-butyl]-benzoic acid methyl ester

The substituted benzoic acid of example 13 is reacted with thionyl chloride into the corresponding acid chloride and further is reacted with methanol in the presence of pyridine into the 3-(2,4-dichlorobenzyloxy)-4-[1-(1-imidazolyl)-butyl]-benzoic acid methyl ester with a melting point of 104° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifica-

What is claimed is:

1. An imidazole of the formula

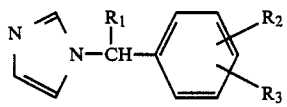

in which

R₁ is hydrogen, a hydrocarbyl radical with 1 to 10 carbon atoms, or a cyclic hydrocarbon radical with 3 to 9 carbon atoms, or a cycloalkylalkyl radical with 4 to 12 carbon atoms or an arylalkyl radical with 7 to 12 carbon atoms, R₂ is a benzyloxy group or benzyloxy substituted with halogen, $C_{1-4}$-alkyl, hydroxyl, methoxy, amino, cyano or combinations thereof, R₃ is a cyano group; an alkanoyl group having 2 to 10 carbon atoms; an alkanoyl group having 2 to 10 carbon atoms which is substituted with halogen, methoxy, amino, hydroxyl, cyano and combinations thereof;

a benzoyl group; a benzoyl group substituted with halogen, $C_{1-4}$-alkyl, methoxy, amino, hydroxyl, cyano or combinations thereof;

a carboxylic group; a carboxylic acid $C_{1-6}$-alkyl ester; a carboxylic acid amide or the corresponding anilide thereof; a mono- or di-$C_{1-6}$-alkylamide; or a saturated heterocyclic amide wherein the nitrogen atom thereof forms a ring of the formula

or a pharmaceutically acceptable salt thereof.

2. A compound according to claim 1:
4-(2,4-dichlorobenzyloxy)-3-[I-(1-imidazolyl)-butyl]-benzonitrile;
{4-(4-bromobenzyloxy)-3-[1-(1-imidazolyl)-butyl]-phenyl}-pentylketone;
4-(4-bromobenzyloxy)-3-[1-(1-imidazolyl)-butyl]benzanilide;
4-(4-bromobenzyloxy)-3-[1-(1-imidazolyl)-butyl]-benzoic acid;
3-(2,4-dichlorobenzyloxy)-4-[1-(1-imidazolyl)-butylbenzonitrile;
3-(2,4-dichlorobenzyloxy)-4-[1-(1-imidazolyl)-butyl]-benzoic acid methyl ester;
3-(2,4-dichlorobenzyloxy)-4-[1-(1-imidazolyl)-butyl]-benzoic acid;
3-(3-bromobenzyloxy)-4-[1-(1-imidazolyl)-butyl]benzonitrile, hydrochloride;
4-(3-bromobenzyloxy)-3-[1-(1-imidazolyl)-butyl]benzonitrile;
3-(4-bromobenzyloxy)-4-[1-(1-imidazolyl)-butyl]-benzoic acid;
3-(4-bromobenzyloxy)-4-[1-(1-imidazolyl)-butyl]benzanilide;
{3-(4-bromobenzyloxy)-4-[1-(1-imidazolyl)-butyl]-phenyl}-pentyl-ketone;
4-(4-bromobenzyloxy)-3-[1-(1-imidazolyl)-butyl]benzonitrile; or
3-(4-bromobenzyloxy)-4-[1-(1-imidazolyl)-butyl]-benzonitrile.

3. A compound of claim 1, wherein R₂ is 3-bromobenzyloxy, 4-bromobenzyloxy, 4-chlorobenzyloxy, 2,3-dichlorobenzyloxy, 2,4-dichlorobenzyloxy, 4,5-dichlorobenzyloxy or 4,6-dichlorobenzyloxy.

4. An aromatose-inhibiting pharmaceutical composition comprising an effective amount of a compound of claim 1 and a pharmaceutically acceptable carrier.

5. An aromatose-inhibiting pharmaceutical composition comprising an effective amount of a compound of claim 2 and a pharmaceutically acceptable carrier.

6. A method of treating estrogen-stimulated tumors in a patient in need of such treatment comprising administering an effective amount of a compound of claim 1.

7. A method according to claim 6, wherein the effective amount if 0.0001–10 mg/kg/day.

8. A method of ameliorating male infertility in a host comprising an effective amount of a compound of claim 1.

9. A method according to claim 8, wherein the effective amount if 0.0001–10 mg/kg/day.

10. A method of inhibiting ovulation comprising administering to a female otherwise capable of ovulation an effective amount of a compound of claim 1.

11. A method according to claim 10, wherein the effective amount is 0.0001–10 mg/kg/day.

12. A method of treating imminent myocardial infarction in a patient in need of such treatment, comprising administering an effective amount of a compound of claim 1.

13. A method according to claim 12, wherein the effective amount is 0.0001–10 mg/kg/day.

* * * * *